US012667498B2

(12) United States Patent
Sablone

(10) Patent No.: US 12,667,498 B2
(45) Date of Patent: Jun. 30, 2026

(54) ABSORBENT SANITARY ARTICLE AND A METHOD FOR PRODUCING THE SAME

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 824 days.

(21) Appl. No.: 17/953,383

(22) Filed: Sep. 27, 2022

(65) Prior Publication Data

US 2023/0099308 A1 Mar. 30, 2023

(30) Foreign Application Priority Data

Sep. 29, 2021 (EP) .................................... 21199940

(51) Int. Cl.
*A61F 13/494* (2006.01)
*A61F 13/15* (2006.01)
*A61F 13/49* (2006.01)

(52) U.S. Cl.
CPC .. *A61F 13/15601* (2013.01); *A61F 13/49011* (2013.01); *A61F 13/49014* (2013.01); *A61F 13/49466* (2013.01)

(58) Field of Classification Search
CPC .......... A61F 13/49011; A61F 13/49012; A61F 13/49014; A61F 13/49058; A61F 13/49466; A61F 2013/49036
See application file for complete search history.

(56) References Cited

U.S. PATENT DOCUMENTS

| 5,540,796 | A | | 7/1996 | Fries | |
| 5,593,401 | A | * | 1/1997 | Sosalla | A61F 13/5644 |
| | | | | | 604/385.28 |
| 5,938,652 | A | * | 8/1999 | Sauer | A61F 13/495 |
| | | | | | 604/386 |
| 6,280,426 | B1 | * | 8/2001 | Turner | A61F 13/49466 |
| | | | | | 604/385.101 |
| 6,336,922 | B1 | * | 1/2002 | VanGompel | A61F 13/49011 |
| | | | | | 604/385.29 |
| 6,506,185 | B1 | | 1/2003 | Sauer et al. | |
| 2002/0173768 | A1 | | 11/2002 | Elsberg et al. | |
| 2003/0050616 | A1 | * | 3/2003 | Reynolds | A61F 13/49466 |
| | | | | | 604/369 |
| 2007/0049895 | A1 | | 3/2007 | Van Gompel et al. | |
| 2012/0277703 | A1 | | 11/2012 | Rhein et al. | |

FOREIGN PATENT DOCUMENTS

| EP | 3811916 A1 | 4/2021 |
| JP | 2016112341 A | 6/2016 |

OTHER PUBLICATIONS

European Search Report dated Apr. 6, 2022. 5 pages.

* cited by examiner

*Primary Examiner* — Catharine L Anderson
(74) *Attorney, Agent, or Firm* — RMCK Law Group PLC

(57) ABSTRACT

An absorbent sanitary article including a chassis and at least one transverse elastic element including in a unitary component an elastic gasketing portion extending between two side edges of the chassis and two elastic side panels extending transversely outwardly beyond respective side edges of the chassis.

10 Claims, 4 Drawing Sheets

ABSORBENT SANITARY ARTICLE AND A METHOD FOR PRODUCING THE SAME

CROSS-REFERENCE TO RELATED APPLICATION

This application claims priority to European Patent Application No. 21199940.4 filed Sep. 29, 2021. The disclosure of the above application is incorporated herein by reference in its entirety.

FIELD OF THE INVENTION

The present invention relates to absorbent sanitary articles, such as, for example, diapers, training pants, absorbent sanitary products for incontinent adults, etc.

The present invention also relates to a method for producing absorbent sanitary articles.

PRIOR ART

An absorbent sanitary article typically has a structure that comprises a central body or chassis having rear and front sections. The chassis normally includes a permeable topsheet intended to come into contact with the user's skin when the article is worn, an impermeable backsheet and an absorbent core sandwiched between the topsheet and the backsheet. The rear and front sections of the chassis are normally closed around the user's waist by means of hook-and-loop fasteners, better known as Velcro® fastening devices.

The rear and front sections may be elasticized. WO 2020/242714 and WO2021/092606 disclose methods for bonding elastic parts under tension to an advancing carrier, which may be used for elasticizing the waist sections of absorbent sanitary articles. The methods disclosed in these documents provide: advancing a carrier substrate, advancing a continuous elastic substrate, cutting an elastic part from the continuous elastic substrate, stretching the elastic part in a cross direction, positioning the elastic part on the carrier substrate, and adhesively bonding a stretched central region of the elastic part with the carrier substrate, and mechanically bonding end regions of the elastic part with the carrier substrate.

US-B1-7252730 discloses a method and apparatus for applying a pair of stretchable outer ears and a gathered stretchable waist band to an absorbent article using a single piece of elastic material which forms both the outer ears and the elastic waist band. The solution disclosed in US-B1-7252730 is advantageous for reducing cost and complexity of the process and converting machines in that the elastic waist bands and the elastic side panels are applied as unitary components. However, there remains a need to provide the absorbent sanitary articles with improved capacity to contain body exudates and to prevent leakage of body exudates from the waist regions.

OBJECT AND SUMMARY OF THE INVENTION

The object of the present invention is to provide an absorbent sanitary article which overcomes the problems of the prior art.

More specifically, an object of the present invention is to provide absorbent sanitary articles which have an improved capacity of retention of body exudates and reduced leakage from the waist regions.

According to the invention, this object is achieved by an absorbent sanitary article having the features of claim 1.

According to another aspect, the invention relates to a method for producing absorbent sanitary articles.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

It should be appreciated that the attached drawings are schematic and not to scale with respect to real products. Various figures may not be represented in the same scale. Also, in various figures some elements may not be shown to better show other elements.

DETAILED DESCRIPTION

Figure 1:
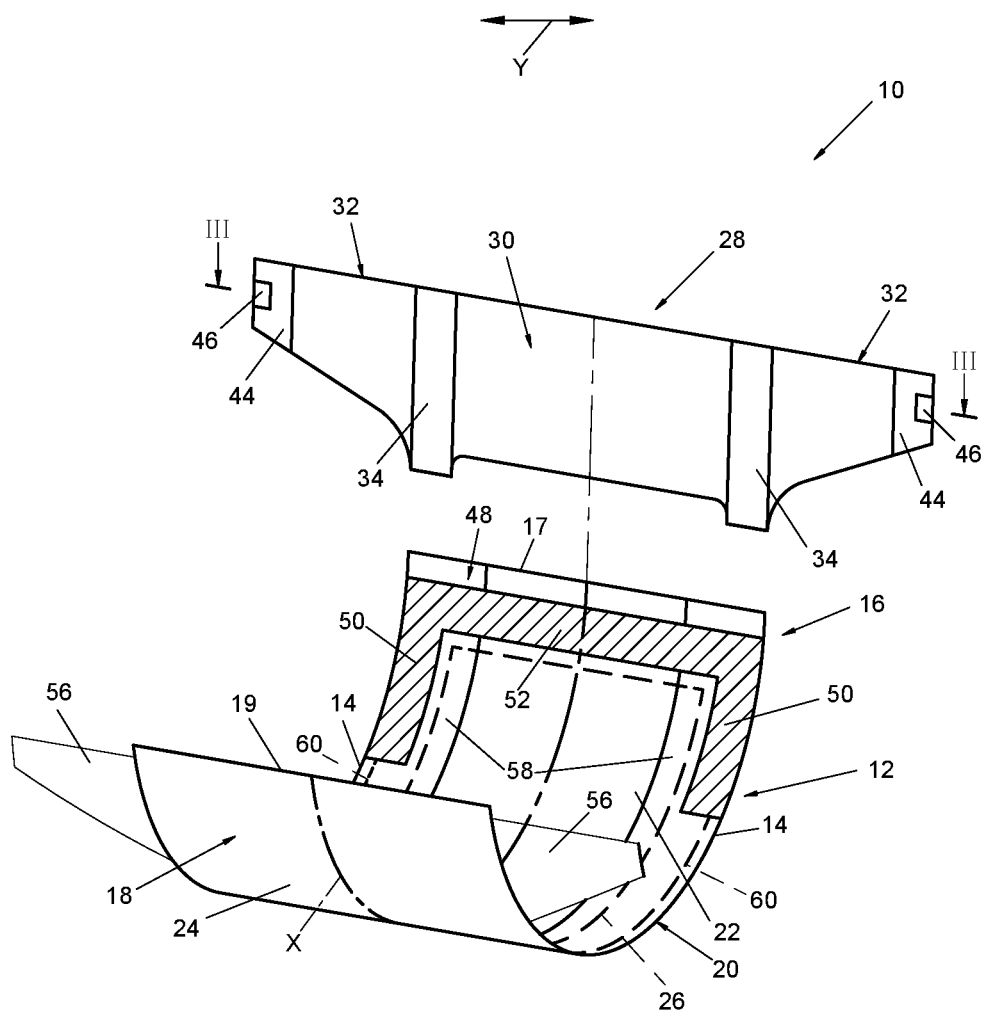
FIG. 1 is a partially exploded perspective view of an absorbent sanitary article according to an embodiment of the present invention.
Figures 2, 3:
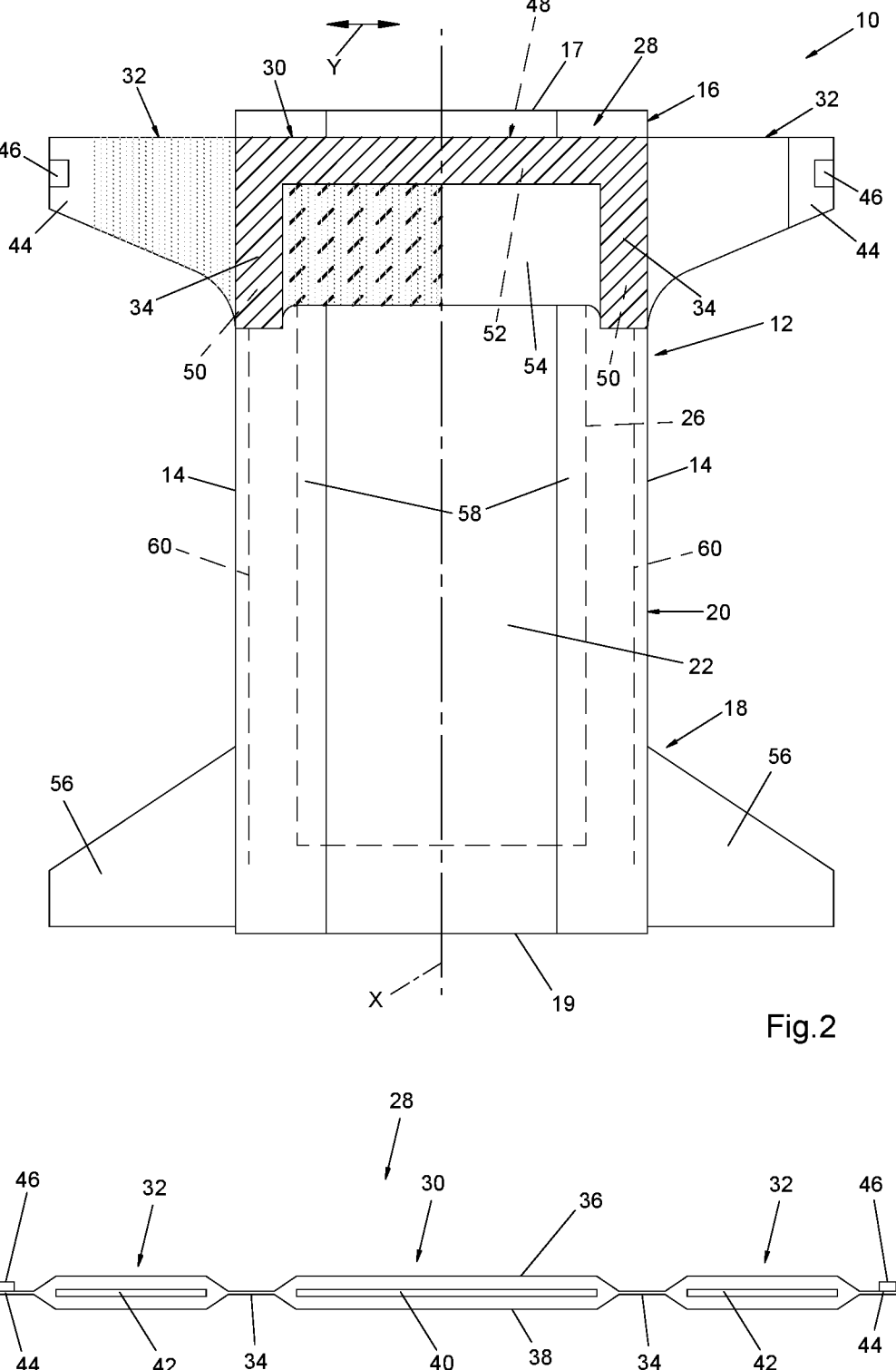
FIG. 2 is a schematic plan view showing the absorbent sanitary article of FIG. 1 in an extended position.
FIG. 3 is a schematic cross-section of a transverse elastic element taken along the line III-III of FIG. 3.

With reference to FIGS. 1 and 2, numeral 10 indicates an absorbent sanitary article according to the present invention. FIG. 1 shows the absorbent sanitary article 10 in the configuration in which it is worn, and FIG. 2 shows the absorbent sanitary article 10 in a flat configuration.

The absorbent sanitary article 10 comprises a chassis 12 elongated along a longitudinal axis X. The chassis 12 has two side edges 14, and rear and front waist sections 16, 18. The rear and front waist sections 16, 18 have respective transverse edges 17, 19. The rear and front waist sections 16, 18 in use are closed around the user's waist. The rear and front waist sections 16, 18 may be not elastic. A crotch section 20 extends between the rear and front waist sections 16, 18. In use, the crotch section 20 is arranged between the legs of the user.

The chassis 12 may have a rectangular shape, with two straight side edges 14 parallel to the longitudinal axis X. In a possible embodiment, the side edges 14 may be shaped to conform to the legs of the user in the configuration in which the absorbent sanitary article 10 is worn, such that in a flat configuration the absorbent sanitary article 10 has substantially an hourglass shape.

The chassis 12 comprises a topsheet 22 made of a permeable material having an outer surface which, in use, is in contact with the user's skin, an impermeable backsheet 24, and an absorbent core 26 set between the topsheet 22 and the backsheet 24.

The absorbent sanitary article 10 comprises at least one transverse elastic element 28 elastically stretchable in a transverse direction Y orthogonal to the longitudinal axis X. In FIG. 1 the transverse elastic element 28 is shown in an exploded position with respect to the chassis 12. The transverse elastic element 28 is applied on the outer surface of the topsheet 22 in at least one of the rear and front waist sections 16, 18. In a possible embodiment, the absorbent sanitary article 10 may comprise rear and front transverse elastic elements 28 attached respectively to the rear and front sections 16, 18 of the chassis 12.

The transverse elastic element 28 includes an elastic gasketing portion 30 and two elastic side panels 32 formed as a unitary component. The elastic gasketing portion 30 extends between the two side edges 14 of the chassis 12 and two elastic side panels 32 extend transversely outwardly beyond respective side edges 14 of the chassis 12.

The transverse elastic element 28 may comprise two non-elastic portions 34, each extending between a respective elastic side panel 32 and the elastic gasketing portion 30.

With reference to FIG. 3, the transverse elastic element 28 may comprise two non-elastic outer layers 36, 38 and at least one transversely stretchable elastic film 40, 42 sandwiched between the two non-elastic outer layers. The transverse elastic element 28 may comprise a central transversely stretchable elastic film 40 extending between the two non-elastic portions 34 and two lateral transversely stretchable elastic films 42 extending laterally outwardly of the respective non-elastic portions 34.

The two non-elastic outer layers 36, 38 may be joined to the transversely stretchable elastic films 40, 42 by ultrasonic welding, thermocompression welding or by glue. In a possible embodiment, the two non-elastic outer layers 36, 38 may be joined to the transversely stretchable elastic films 40, 42 by a pattern of ultrasonic spot welds. The spot welds may form through holes in the transversely stretchable elastic films 40, 42 and the two non-elastic outer layers 36, 38 may be fixed to each other through the through holes. In the non-elastic portions 34 the transversely stretchable elastic films 40, 42 are not present and the two non-elastic outer layers 36, 38 are fixed directly to each other.

The two elastic side panels 32 may have respective non-elastic distal portions 44 carrying respective fastening formations 46, e.g. micro-hook fastening formations.

The transverse elastic element 28 may comprise a non-elastic outer layer 36 of non-woven material and a non-elastic outer layer 38 of impermeable plastic material. The non-elastic outer layer 38 of impermeable plastic material may forms the surface of the elastic gasketing portion 30 facing the outer surface of the topsheet 22. The non-elastic outer layer 36 of non-woven material may form the surface of the elastic gasketing portion 30 which in use is in contact with the user's skin.

In a possible embodiment, the elastic gasketing portion 30 and the two elastic side panels 32 may have different transverse elasticity. The elasticity may be expressed by the percentage difference between the dimension of an element in a condition of maximum elongation and at rest. In a possible embodiment, each of the two elastic side panels 32 may have a transverse elasticity comprised between 160-200%. In a possible embodiment, the elastic gasketing portion 30 may have a transverse elasticity comprised between 50-100%. The different elasticity between the elastic gasketing portion 30 and the two elastic side panels 32 may be obtained by providing elastic films 40, 42, with different elastic properties and/or by providing different welding patterns between the elastic films 40, 42 and the non-elastic outer layers 36, 38.

With reference to FIG. 1, the or each transverse elastic element 28 is attached to the rear and/or front waist section 16, 18 the chassis 12 along a C-shaped attachment profile 48 including two opposite longitudinal portions 50 adjacent to respective side edges 14 of the chassis 12 and a transverse outer portion 52 adjacent to one of said rear and front transverse edges 17, 19 of the chassis 12.

Figure 6:
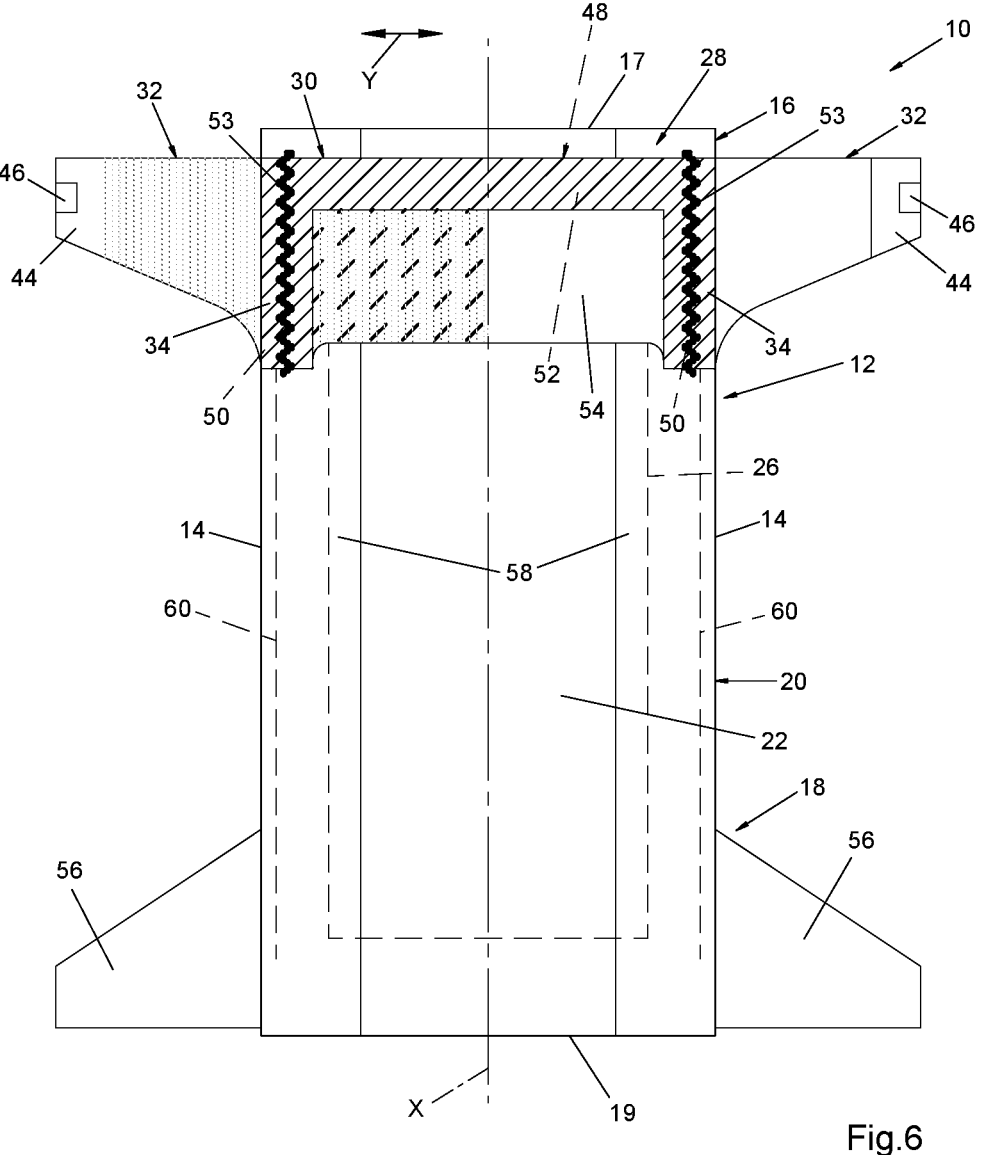
FIG. 6 is schematic plan view showing a variant of the absorbent sanitary article of FIG. 2 in an extended position.

The C-shaped attachment profile 48 may be formed by glue or by welding or a combination thereof. With reference to FIG. 6, in a possible embodiment, the transverse outer portion 52 of the C-shaped attachment profile 48 may be formed by glue and the two opposite longitudinal portions 50 may be formed by welding 53, e.g. ultrasonic welding. In a possible embodiment, the two opposite longitudinal portions 50 of the C-shaped attachment profile 48 may include both glue and welding 53.

The two non-elastic portions 34 of the transverse elastic element 28 may be overlapped to the two opposite longitudinal portions 50 of the C-shaped attachment profile 48.

With reference to FIG. 2, a central inner region 54 of the elastic gasketing portion 30 is detached from the outer surface of the topsheet 22 to form a pocket open toward the crotch section 20. The central inner region 54 of the elastic gasketing portion 30 is bordered on three sides by the C-shaped attachment profile 48 and is unattached on the edge opposite the transverse outer portion 52.

The absorbent sanitary article 10 may comprise a pair of front side panels 56 projecting laterally beyond the side edges 14 of the front section 16. The front side panels 56 may have a surface of loop material (e.g. a non-woven material) for connection with the micro-hook fastening formations 46 of the elastic side panels 32.

The absorbent sanitary article 10 may comprise a pair of elastic leg cuffs 58. The elastic leg cuffs 58 may comprise a plurality of elastic wires which are fixed, e.g. by glue, at discrete points to two opposite non-woven layers. The absorbent sanitary article 10 may also comprise leg elastic elements 60 which may be formed by stretched elastic wires fixed between the topsheet 22 and the backsheet 24 and extending along the side edges 14 of the chassis 12, which impart a pleated form to the side edges 14 in the crotch section 20.

When the absorbent sanitary article is worn, the or each transverse elastic element 28 is in contact with the back and/or front waist regions of the user. The elastic side panels 32 close the rear and front sections 16, 18 of the chassis 12 around the user's waist. The outer layer 36 of the elastic gasketing portion 30 is kept in contact with the user's skin. The outer layer 36 of the elastic gasketing portion 30 may be formed by a layer of non-woven material to provide a soft feeling against the user's skin.

The central inner region 54 of the elastic gasketing portion 30 forms an inwardly open pocket between the outer surface of the topsheet 22 and the elastic gasketing portion 30. Such pocket helps containing liquid, solid or semi-solid body exudates in the back and/or front waist region. The outer layer 38 of the elastic gasketing portion 30 facing the topsheet 22 may be of impermeable plastic material to form an impermeable barrier which helps containing body exudates in said pocket.

The elastic leg cuffs 58 may draw inwardly the inner edge of the elastic gasketing portion 30 to distance the inner surface of the elastic gasketing portion 30 from the topsheet 22, which has the effect of opening the pocket.

Figure 4:
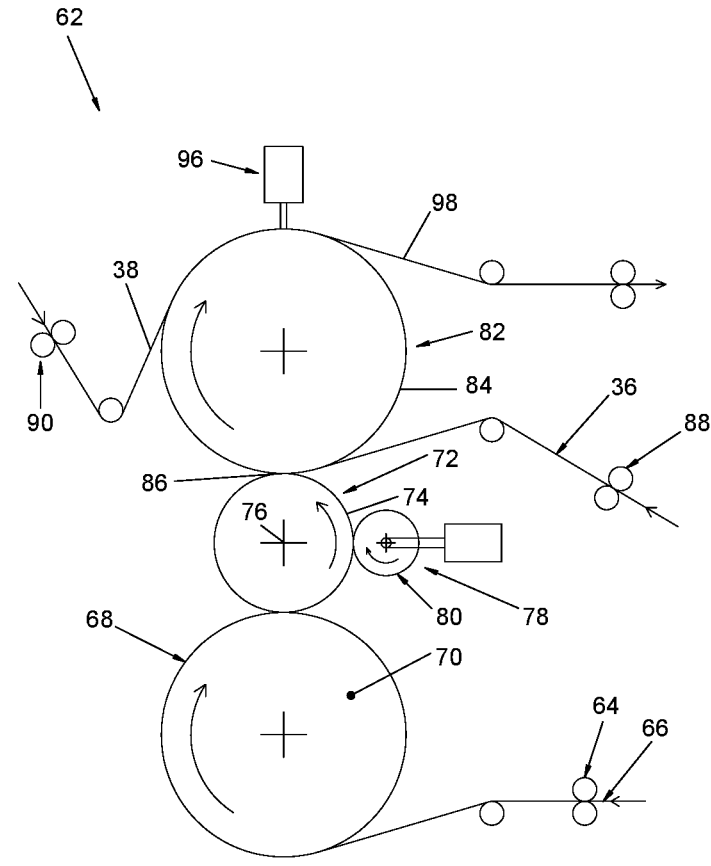
FIG. 4 is a schematic side view of an embodiment of an apparatus for producing a continuous elastic laminate.

The transverse elastic elements 28 of the absorbent sanitary articles 10 according to the present invention may be manufactured by an apparatus 62 schematically shown in FIG. 4.

The apparatus 62 comprises a first feeding device 64 configured to feed a continuous elastic film 66 in a direction parallel to its longitudinal axis.

The apparatus 62 comprises a spreader device 68 configured to stretch the continuous elastic film 66 in a direction transverse to its longitudinal axis. The spreader device 68 comprises two discs 70 rotatable about respective axes inclined with respect to each other. The discs 70 have respective circumferential edges provided with means for gripping respective side edges of the continuous elastic film 66. The discs 70 may be provided on their circumferential edges with holes connected to a source of sub-atmospheric pressure for gripping the side edges of the elastic film 66 by suction. The circumferential edges of the discs 70 may be provided with protruding pins that engage the side edges of the elastic film 66 alternatively or in addition to the vacuum gripping means.

The spreader device 68 picks up the continuous elastic film 66 in a gripping zone with a first width and releases the continuous elastic film 66 in an application zone with a second width larger than the first width. In the path from the gripping zone to the application zone the elastic film 66 is therefore elastically stretched in a direction transverse to the longitudinal axis.

The apparatus 62 comprises a transfer wheel 72 having an outer cylindrical surface 74 and rotatable about an axis of rotation 76. The transfer wheel 72 is provided with gripping elements, e.g. suction holes, configured to hold the transversally stretched continuous elastic film 66 on the outer cylindrical surface 74. The spreader device 68 applies the transversally stretched continuous elastic film 66 on the outer cylindrical surface 74 of the transfer wheel 72, where it is held stretched in the transverse direction.

The apparatus 62 comprises a longitudinal cutting device 78 configured to cut the transversally stretched continuous elastic film 66 held on the outer cylindrical surface 74 of the transfer wheel 72 along two parallel longitudinal cutting lines, to split the continuous elastic film 66 in three parallel continuous elastic films 40, 42 (FIG. 3), which are held in a transversally stretched state on the outer cylindrical surface 74 of the transfer wheel 72. The longitudinal cutting device 78 may comprise two parallel cutting disks 80 rotating about a common axis parallel to the axis of rotation 76 of the transfer wheel 72. The cutting disks 80 may cooperate with respective circumferential slots formed on the outer cylindrical surface 74 of the transfer wheel 72.

After the longitudinal cut of the continuous elastic film 66, the three parallel continuous elastic films 40, 42 partially contract in the transverse direction Y, so that the three parallel continuous elastic films 40, 42 are spaced apart from each other in the transverse direction Y. The transverse contraction of the three parallel continuous elastic films may be obtained by not providing gripping elements (e.g. suction holes) on portions of the outer cylindrical surface 74 of the transfer wheel 72 adjacent to the cutting lines, so that lateral portions of the three parallel continuous elastic films adjacent to the cutting lines are not retained on the outer cylindrical surface 74 of the transfer wheel 72 and contract elastically.

The apparatus 62 comprises an anvil wheel 82 rotatable about an axis of rotation parallel to the axis of rotation 76 of the transfer wheel 72. The anvil wheel 82 has an outer cylindrical surface 84 provided with holes pneumatically connected to a source of sub-atmospheric pressure. The outer cylindrical surface 84 of the anvil wheel 82 is tangent to the outer cylindrical surface 74 of the transfer wheel 72 in a transfer zone 86.

The apparatus 62 comprises second and third feeding devices 88, 90 configured to feed to the anvil wheel 82 first and second continuous non-elastic layers 36, 38, respectively upstream and downstream of the transfer zone 86.

In the transfer zone 86 the three parallel continuous elastic films 40, 42 are transferred from the transfer wheel 72 to the anvil wheel 82. On the anvil wheel 82 the three parallel continuous elastic films are sandwiched between the continuous non-elastic layers 36, 38 while held transversally stretched.

The apparatus 62 comprises a fastening device 96 cooperating with the outer cylindrical surface 84 of the anvil wheel 82. The fastening device 96 may be an ultrasonic welding device, a pressure device for fastening by adhesive, or a thermal or thermomechanical welding device. The fastening device 96 joins the transversally stretched three parallel continuous elastic films 40, 42 to the continuous non-elastic layers 36, 38 to form a continuous elastic laminate 98 which is then detached from the anvil wheel 82.

Downstream of the fastening device 96 the continuous elastic laminate 98 has in a cross section the shape schematically illustrated in FIG. 3, comprising three continuous elastic films 40, 42 enclosed between two continuous non-elastic layers 36, 38, and anchored to the continuous non-elastic layers 36, 38, e.g. by a pattern of connecting points. The continuous elastic laminate 96 has two continuous non-elastic portions 34 wherein the elastic films 40, 42 are spaced apart from each other and the two continuous non-elastic layers 36, 38 are directly fixed to each other. The continuous elastic laminate 96 has also non-elastic lateral portions 44 where the non-elastic layers 26, 38 are directly fixed to each other. Fastening formations 46 may be applied on the non-elastic lateral portions 44 in longitudinally spaced positions while the continuous elastic laminate 98 is held on the anvil wheel 82.

Figure 5:
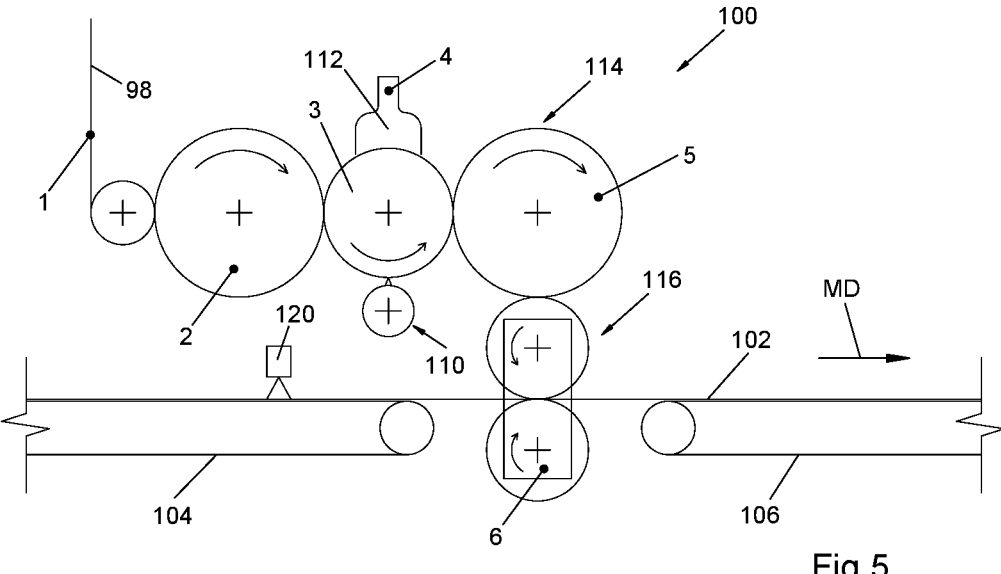
FIG. 5 is a schematic side view of an embodiment of a machine for manufacturing absorbent sanitary articles according to the present invention.

FIG. 5 schematically shows a machine 100 for manufacturing absorbent sanitary products.

The machine 100 is configured for forming an array of chassis 12. In the machine 100 the array of chassis 12 may be formed in the form of a continuous composite tape 102 which advances in a machine direction MD, on conveyors 104, 106.

With reference to FIG. 5, the continuous elastic laminate 98 exiting the apparatus 62 of FIG. 4 may be supplied in-line to the machine 100 for manufacturing absorbent sanitary articles.

Alternatively, at the exit of the apparatus 62 of FIG. 4 the continuous elastic laminate 98 may be collected in reels which are stored and transported to machines 100 for manufacturing absorbent sanitary articles. In this case, the continuous elastic laminate 98 which supplies the machine 100 is unwound from a reel in an unwinding device (not shown).

With reference to FIG. 5, in the machine 100 the continuous elastic laminate 98, provided either in-line or unwound from a reel, is transversely stretched in a stretching device 108 comprising two disks rotating about respective axes inclined with respect to each other.

The transversely stretched continuous elastic laminate 98 is transversely cut in a cutting unit 110 to form individual transverse elastic elements 28. The cutting unit 110 may be configured to form individual transverse elastic elements 28 with a shaped profile as shown in FIGS. 1 and 2. Wastes produced by cutting the transverse elastic elements 28 along shaped profiles may be collected by a waste collecting device 112.

At the exit of the cutting unit 110 the transverse elastic elements 28 are spaced apart from each other in a longitudinal direction by a repitch unit 114.

The repitch unit 114 transfers the longitudinally spaced transverse elastic elements 28 to a welding unit 116 comprising a pair of counter-rotating welding rollers 118 forming a gap in which the continuous composite tape 102 advances. The welding unit 116 applies the individual transverse elastic laminates 28 to respective chassis 12 in at least one of the rear and front waist sections 16, 18.

A glue dispenser 120 may be provided for intermittently dispensing glue layers on the continuous composite tape 102 upstream of the welding unit 116.

The individual transverse elastic elements 28 are attached to the array of chassis 12 such that the elastic gasketing portion 30 of each transverse elastic element 28 extends between the two side edges 14 of the respective chassis 12 and the two elastic side panels 32 extend transversally outwardly beyond respective side edges 14 of the respective chassis 12.

The individual transverse elastic elements 28 are attached to the array of chassis 12 along respective C-shaped attachment profiles. This attachment may be formed by glue on the transverse outer portions 52 and by welding, e.g. ultrasonic welding, on the opposite longitudinal portions 52 of the C-shaped attachment profile 48.

Of course, without prejudice to the principle of the invention, the details of construction and the embodiments can be varied, even significantly, with respect to those illustrated here without departing from the scope of the invention as defined by the following claims.

The invention claimed is:

1. An absorbent sanitary article comprising:
   a chassis having a longitudinal axis, two side edges, rear and front transverse edges, rear and front waist sections, and a crotch section intermediate between the rear and front waist sections, the chassis including a topsheet having an outer surface which in use is adapted to be in contact with a user's skin, a backsheet, and an absorbent core set between the topsheet and the backsheet, and
   at least one transverse elastic element applied on the outer surface of the topsheet in at least one of said rear and front waist sections, the at least one transverse elastic element comprising in a unitary component:
      an elastic gasketing portion elastically stretchable in a transverse direction orthogonal to said longitudinal axis and extending between the two side edges of the chassis,
      two elastic side panels elastically stretchable in said transverse direction and extending transversally outwardly beyond respective side edges of the chassis, and two non-elastic portions each extending between a respective elastic side panel and the elastic gasketing portion,
   wherein the at least one transverse elastic element is attached to the chassis along a C-shaped attachment profile including two opposite longitudinal portions adjacent to respective side edges of the chassis and a transverse outer portion adjacent to one of said rear and front transverse edges of the chassis,
   wherein a central inner region of the elastic gasketing portion is detached from the outer surface of the topsheet to form a pocket open toward said crotch section, and
   wherein said elastic gasketing portion and said two elastic side panels have different transverse elasticity.

2. The absorbent sanitary article of claim 1, wherein said two non-elastic portions are overlapped to said two opposite longitudinal portions of said C-shaped attachment profile.

3. The absorbent sanitary article of claim 1, wherein the at least one transverse elastic element comprises a central transversally stretchable elastic film extending between said two non-elastic portions and two lateral transversally stretchable elastic films extending laterally outwardly of the respective non-elastic portions.

4. The absorbent sanitary article of claim 1, wherein each of said two elastic side panels has a transverse elasticity comprised between 160-200% and wherein said elastic gasketing portion has a transverse elasticity comprised between 50-100%.

5. The absorbent sanitary article of claim 1, wherein said at least one transverse elastic element is attached to the chassis by glue along said transverse outer portion and by welding and/or glue along said two opposite longitudinal portions.

6. The absorbent sanitary article of claim 1, wherein said two elastic side panels have respective non-elastic distal portions carrying respective fastening formations.

7. The absorbent sanitary article of claim 1, wherein said at least one transverse elastic element comprises an outer layer of impermeable plastic material.

8. The absorbent sanitary article of claim 7, wherein said outer layer of impermeable plastic material forms a surface of the elastic gasketing portion facing the outer surface of the topsheet.

9. The absorbent sanitary article of claim 1, wherein said at least one transverse elastic element comprises at least one layer of non-woven material.

10. The absorbent sanitary article of claim 9, wherein said at least one layer of non-woven material forms a surface of the elastic gasketing portion which in use is adapted to be in contact with the user's skin.

\* \* \* \* \*